(12) United States Patent
Lin et al.

(10) Patent No.: US 7,675,626 B2
(45) Date of Patent: Mar. 9, 2010

(54) METHOD OF DETECTING DRUG RESISTANT MICROORGANISMS BY SURFACE PLASMON RESONANCE SYSTEM

(75) Inventors: Chi-Hung Lin, Taipei (TW); How-Foo Chen, Taipei (TW); Ya-Ling Chiang, Taipei (TW)

(73) Assignee: National Yang Ming University, Taipei (TW)

( * ) Notice: Subject to any disclaimer, the term of this patent is extended or adjusted under 35 U.S.C. 154(b) by 612 days.

(21) Appl. No.: 11/582,387

(22) Filed: Oct. 18, 2006

(65) Prior Publication Data

US 2008/0096241 A1    Apr. 24, 2008

(51) Int. Cl.
G01N 21/55    (2006.01)

(52) U.S. Cl. .................. 356/445; 356/448; 422/82.05

(58) Field of Classification Search ............. 356/445, 356/448; 422/82.05
See application file for complete search history.

(56) References Cited

OTHER PUBLICATIONS

Backman, V., L. T. Perelman et al., "Detection of Preinvasive Cancer Cells" Nature 2000, vol. 406, p. 35-36.

Arimoto, H., T. Oishi et al., "Affinity of a Vancomycin Polyumer With Bacterial Surface Models" Tetrahedron Letters 2001, vol. 42, p. 3347-3350.

Chen, K. H., C.C. Hsu et al., "Measurement of Wavelength Shift by Using Surface Plasmon Resonance Heterodyne Interferometry" Optics Communications 2002, vol. 209, p. 167-172.

Chien, F.C., K.T. Huang et al., "Direct Detection of the Interaction of Tiny Analytes With Receptors Using An Advanced Plasmonic Biosensor" Plasmonics in Biology and Medicine II 2005, vol. 5703, p. 107-117.

Choi, J,W., K.W. Park et al., "Cell Immobilization Using Self-Assembled Synthetic Oligopeptide and Its Application to Biological Toxicity Detection Using Surface Plasmon Resonance" Biosensors and Bioelectronics 2005, vol. 20, p. 2300-2305.

*Primary Examiner*—Tarifur Chowdhury
*Assistant Examiner*—Tara S Pajoohi
(74) *Attorney, Agent, or Firm*—WPAT, P.C.; Anthony King

(57) ABSTRACT

The present invention provides a method for detecting a drug resistant microorganism by surface plasmon resonance (SPR). Values of SPR angle shift (V) and the drop of SPR angle shift (D) of control group (V1 and D1) and sample (V2 and D2) can determine the microorganism is drug resistant by identifying (I) ration of V1/V2 larger than 1.001, (II) ration of D1/D2 larger than 1.001 and (III) the SPR angle shift of the sample more smooth or monotonic that that of the control. The present invention further provides SPR as a device used for the method of the present invention.

17 Claims, 14 Drawing Sheets

ND OF DETECTING DRUG
METHOD OF DETECTING DRUG RESISTANT MICROORGANISMS BY SURFACE PLASMON RESONANCE SYSTEM

FIELD OF THE INVENTION

The present invention relates to a method and a device for detecting a drug resistant microorganism by surface plasmon resonance (SPR).

BACKGROUND OF THE INVENTION

It is necessary to use antibiotics to treat patients, and this method has been commonly used in every big hospital. However, under the excessive use of antibiotics, drug resistance of bacteria has gradually increased. Therefore, when patients are infected or being ill, it is important to distinguish whether this microorganism is susceptible or resistant to antibiotics that are used to treat patients. Besides, the application for detection of drug resistance in human infection diseases, fast detection of drug resistance of microorganisms is also very important in the field of agriculture.

Cells can be separated into two fundamentally different types: eukaryotic and prokaryotic cells. Bacteria belong to prokaryote. The essential components of bacteria include cell wall composed of peptidoglycan that gives rigid support and protects cell against osmotic pressure, cytoplasm that is the site of transport and oxidative, ribosome that serves as the site of mRNA translation, and chromosome that is the genetic material passed generation to generation. There are also some nonessential components like capsule which protects cells from phagocytosis, flagellum that increases the motility of cells, pilus or fimbria that provides the adherence to cell surface and the attachment to bacteria during conjugation, and plasmid that contains a variety of genes for antibiotic resistance and enzymes.

*Escherichia coli* is a gram-negative rod, about 3-5 μm*0.5 μm. *Escherichia coli* lives in gut where it helps to digest food and produces Vitamin K. *E. coli* causes a variety of diseases both within and outside the intestinal tract by pili, capsule, endotoxin and exotoxins. The most common diseases caused by *E. coli* is urinary tract infection, gram-negative rod sepsis, neonatal meningitis and the agent most frequently associated with traveler's diarrhea.

Penicillin acts by inhibiting transpeptidase, the enzymes that catalyze the final cross-linking step in the synthesis of peptidoglycan. Penicillin-treated cells die by rupture as a result of the influx of water causing the high-osmotic-pressure interior of the bacterial cell, and ampicillin has activity against several gram-negative rods that the earlier penicillin did not have. The damage of bacteria cell wall caused by antibiotics changes the compartment and shape of bacteria thus alternates the refractive index of bacteria.

There are three mechanisms that mediate bacterial resistance to drugs. (i) Bacteria produce enzymes that inactivate the drug, for example, β-lactamase, which can inactivate penicillin by cleaving the β-lactam ring of drugs. (ii) Bacteria with mutant protein on the ribosomal can result in resistance to streptomycin. (iii) Bacteria can change their permeability so that the drug effect on intracellular concentration can not work. Drug resistance of most bacteria is due to genetic change, chromosomal mutation, or transformation of plasmid. The frequency of spontaneous mutation, usually ranging from $10^{-7}$ to $10^{-9}$, is much lower than that of acquisition of resistance plasmid. In this case, when it comes to clinical problem, chromosomal resistance occurs less than plasmid-mediated resistance.

Surface plasmon was first predicted by Ritchie in 1957 and verified by Powell and Swan in 1960. Optical surface plasmon resonance (SPR) was not demonstrated until 1968 by Otto. Ever since, SPR is widely applied to the study of bio-material process including immunodiagnostics and kinetic analysis of antibody-antigen interactions, and also provides valuable dynamic information which includes gas adsorption, binding kinetics, epitope mapping, and film thickness measurements.

Although some prior art (1) Backman, V., L. T. Perelman, et al. (2000). "Detection of preinvasive cancer cells." *Nature* 406(6791):35; (2) Arimoto, H., T. Oishi, et al. (2001). "Affinity of a vancomycin polymer with bacterial surface models." *Tetrahedron Letters* 42(19): 3347-3350; (3) Chen, K. H., C. C. Hsu, et al. (2002). "Measurement of wavelength shift by using surface plasmon resonance heterodyne interferometry." *Optics Communications* 209(1-3): 167; (4) Chien, F. C., K. T. Huang, et al. (2005). *Direct detection of the interaction of tiny analytes with receptors using an advanced plasmonic biosensor*. Progress in Biomedical Optics and Imaging—Proceedings of SPIE; and (5) Choi, J. W., K. W. Park, et al. (2005). "Cell immobilization using self-assembled synthetic oligopeptide and its application to biological toxicity detection using surface plasmon resonance." *Biosensors and Bioelectronics* 20(11): 2300-2305, have provided some progress, some defects of the prior art need to be modified.

DETAILED DESCRIPTION OF THE INVENTION

Figure 1:
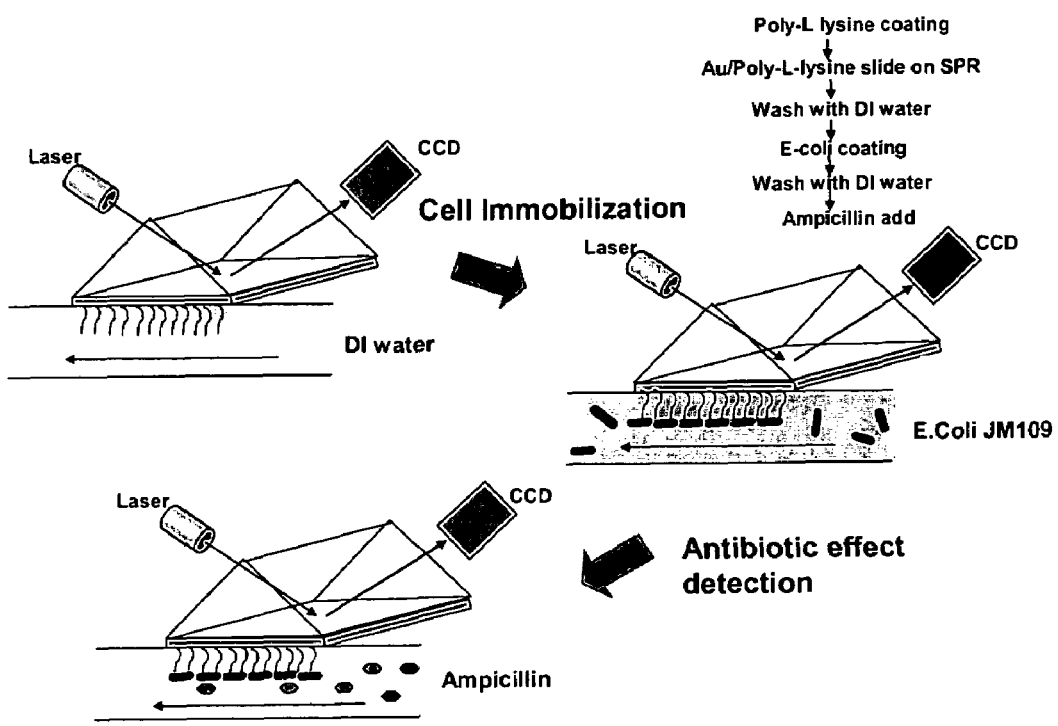
FIG. 1 shows the brief illustration of the method of the present invention.

Unless defined otherwise, all technical and scientific terms used herein have the same meaning as commonly understood by one of ordinary skill in the art to which this invention belongs. Although any methods or materials similar or equivalent to those described herein can be used in the practice or testing of the present invention, the preferred methods and materials are described.

There are four major sites in bacterial cells that are sufficiently different from human cells, and they serve as the basis for the action of clinically effective drugs:

(A). Inhibition of Cell Wall Synthesis

Drugs like penicillin, cephalosporin, impenem, aztreonam are designed to inhibit cell wall synthesis which works on the inhibition of cross-linking (transpeptidation) of peptidoglycan or other developing steps of peptidoglycan.

(B). Inhibition of Protein Synthesis

Drugs like chloramphenicol, tetracyclines and aminoglycosides are designed to work on the inhibition of protein synthesis, and they mainly act on 50S and 30S ribosomal subunit.

(C). Inhibition of Nucleic Acid Synthesis

There are mainly three kinds of working principles. Drugs like Sulfonamides and trimethoprim are used to block nucleotide synthesis. Nalidixic acid and quinolones are used to block DNA synthesis. Rifampin is used to block mRNA synthesis.

(D) Alternation of Cell Membrane Function

Drug designed to work on alternation of cell membrane function is Polymyxin.

The surface plasmon resonance (SPR) phenomenon appears from the energy coupling into the metal film via coupling system. The SPR angle will change with different refractive index of samples. There are several advantages of SPR system: no labeling required, providing real-time information, using small sample volumes, and very high sensitivity.

Ampicillin is the antimicrobial drug chosen in this embodiment which works on the inhibition of cell wall synthesis, because surface plasmon resonance excites surface plasmon in about ~200 nm deep. The mechanism of action of ampicillin is on inhibiting transpeptidases, the enzyme catalyzes the final cross-linking step in the synthesis of peptidoglycan. For example, in *Staphylococcus aureus*, transpeptidation occurs between the amino group on the end of pentaglycine cross-link and the terminal carboxyl group of the D-alanine on the tetrapeptide side chain. Since the stereochemistry of penicillin is similar to that of a dipeptide, D-alanyl-D-alanine, it can bind to the active site of the transpeptidase and inhibit its activity.

There are two additional factors involved in the action of penicillin. The first is that penicillin binds to a variety of receptors in the bacterial cell membrane or cell wall called penicillin-binding proteins (PBPs). Some PBPs are transpeptidases, and the characteristics of others are unknown. Changes in PBPs are in part responsible for an organism of becoming resistant to penicillin. The second factor is autolytic enzyme called murein hydrolase (murein is a synonym for peptidoglycan) activated in penicillin-treated cells and degrading the peptidoglycan. Some strains of *S. aureus* are tolerant to the action of penicillin since these autolytic enzymes are not activated. A tolerant organism is the one inhibited but not killed by a usual bactericidal drug, such as penicillin. Penicillin-treated cells die by rupture as a result of the influx of water to cause the high-osmotic-pressure in interior of the bacterial cell. The osmotic pressure of the medium is raised about three folds.

Penicillin is bactericidal, but it kills cells only when they are proliferating. When cells are proliferating, new peptidoglycan is synthesized and transpeptidation occurs. However, in nongrowing cell, no new cross-linkages are required and penicillin is inactive. Penicillin is called β-lactam drug because of the importance of the β-lactam ring. An intact ring structure is essential for antibacterial activity. Cleavage of the ring by penicillinase (also called β-lactamase) inactivates the drug. The effectiveness of penicillin against gram-negative rods has been increased by a series of chemical changes on the side chain. It can be seen that ampicillin has activity against several gram-negative rods, such as *Escherichia coli*.

There are two common ways used in clinical laboratories to test the sensitivity of bacteria to antibiotics, the disc diffusion technique and the tube dilution technique. The disc diffusion technique is to place disks with various antibiotics on the plate which has been inoculate with organism, the result will be reported after incubating at 35° C. for 18-24 hours, but the result is not precise enough.

The tube dilution technique is to dilute antibiotics solution into various concentrations, and then culture organisms with the same amount. The result is observed after incubating at 35° C. for 18 hours. But this technique consumes time, energy, and money, so it is always used to test organisms with a slow growing rate.

Basic Principles of Surface Plasmon Resonance Biosensor

The surface plasmon is mainly located on the surface of metal, as the oscillation of electrons caused by the absorption of energy at the interface between the metal and the dielectrics. The condition of SPR is obtained by matching the boundary condition between the metal and the dielectrics and by matching the optical phase along the boundary. Considering the electrons on metal as electron gas, the dispersion relation must be $$ksp=(\omega/c)[(\epsilon_m \epsilon_d)/(\epsilon_m+\epsilon_d)]^{1/2}=k_x, \text{ where}$$

ksp: wave vector of the surface plasmon wave c: speed of light $\epsilon_m$: dielectric constant of metal $\omega$: optical frequency $\epsilon_d$: dielectric constant of dielectric;

This condition indicates that the electromagnetic wave in the dielectrics and the surface plasmon wave on the surface of the metal must match on the wave vector and on the optical frequency. The match on the wave vector along the metal-dielectrics interface is considered as momentum conservation; The match on the optical frequency is considered as energy conservation. Under the normal situation; however, the wave vector of surface plasmon is larger than the wave vector of injection light. The wave vector of injection light must be increased to match that of the surface plasmon wave. There are two methods to increase the wave vector and achieve the match condition: One is through a grating coupler and the other is through an attenuated total reflection (ATR) coupler.

For the grating coupled systems, a grating structure is integrated into the side, opposite to the dielectrics, of metal to provide an additional wave vector. The match condition is then $$k_{sp} = \frac{\omega}{c}\sqrt{\frac{\varepsilon_d \varepsilon_m}{\varepsilon_d + \varepsilon_m}} = \frac{\omega}{c}\sin\theta_0 \pm vg = k_x,$$

where ν is the order of the grating diffraction, g=2π/a with a the grating constant, and $\theta_0$ is the incident angle of the light, said the laser beam.

For the ATR systems, the additional wave vector is provided by a prism attached to the side, opposite to the dielectrics, of the metal. The match condition provides that $$k_{sp}=k_x=k_{np}\sin\theta_{sp},$$

where the index np indicates the refractive index of the prism. The $\theta_{sp}$ is the resonance angle, by which most of the energy of the laser beam will couple into the surface plasmon. When this occurs, we called this coupling reaching resonance. It is then named as the surface plasmon resonance. When the refractive index of the dielectrics changes, the resonance angle shifts. Therefore, the detection of the resonance angle shift can determine the change of the refractive index of the dielectrics. Alternatively, change of the refractive index also affects the optical phase of the laser beam after reflected from the metal-dielectrics interface. Therefore, the refractive index change can also be detected by interferometry methods, which measure the shift of this optical phase and then determine the amount of the refractive index change.

The prism based system of SPR can be applied in different configurations. In the Otto arrangement there is a distance between the metal and the TIR surface. The space is filled with a lower refractive index medium. This configuration is useful in the study of SPR in solid phase media. However since the distance between metal and TIR surface reduces the SPR efficiency, it is less useful for applications with solutions. In the Kretchman configuration, the metal layer is directly on top of the TIR surface enabling a more efficient plasmon generation. A third configuration looks like the Otto arrangement but uses a special layer to enhance TIR. The coupling of the TIR light to plasmon is done by the resonant mirror (RM) principle. On a prism in which the light is in TIR a small layer of silica (~1 mm) is deposited. On top of the silica, there is a titanium layer. The silica layer is thin enough to allow the evanescent field generated by the prism to couple into the high refractive index titanium. This is so called frustrated total internal reflection (FTIR) allows the titanium layer to function as an optical waveguide. Repeated total internal reflection of the guided mode within the wave guiding titanium layer results in the production of an evanescent field at the titanium-adlayer interface. The exact angle of incident light at which the resonance between the wave guided mode and the evanescently coupled light occurs is directly dependent upon the refractive index of the surface adlayer. Unlike the SPR device however, there is virtually no loss of the reflected light intensity associated with the resonance condition. Rather, resonance is accompanied via a 2 pi change in phase of the reflected light, which is recorded interferometrically.

The present invention is related to a method of detecting a microorganism sensitive to a drug by a surface plasmon resonance device comprising (a) a prism coated with a metal film on the bottom of the prism or a metal film with grating, (b) a chamber for flowing through the microorganism wherein the chamber is contacted with the film, (c) an immobilized material coated on the inner layer of the chamber, (d) a light source which is projected on the film to generate an output light, (e) a light detector to receive the output light, and (f) a device to analysis surface plasmon resonance angle shift, the method comprises (1) providing a sample and a control group wherein the control group is drug susceptible or wild type, (2) flowing the control group and the sample through the chamber respectively to be captured by the immobilized material, (3) adding the drug into the chamber, (4) recording the data selected from the group consisting of (i) the value V1 of surface plasmon resonance angle shift of the control group and the value V2 of surface plasmon resonance angle shift of the sample, (ii) the value D1 of the drop of surface plasmon resonance angle shift of the control group and the value D2 of the drop of surface plasmon resonance angle shift of the sample, and (iii) the surface plasmon resonance angle shift of the control group and the sample, and (5) identifying the sample as drug resistance by the record selected from the group consisting of (1) ratio of V1/V2 larger than 1.001, (II) ratio of D1/D2 larger than 1.001, and (III) the surface plasmon resonance angle shift of the sample more smooth or monotonic than that of the control.

The microorganism of this invention is bacteria or cell. The preferred embodiment of the bacteria is *E. coli* or *Staphylococcus aureus*. The drug mentioned-above is penicillin, cephalosporin, ampicillin, chloramphenicol, tetracycline, sulfonamide or polymynix. The preferred embodiment is ampicillin.

The immobilized material of this invention is poly-L-lysine, antibody, or oligopeptide and the metal film mentioned-above is golf film.

The light source of this invention is He—Ne Laser with 632.8 nm wavelength.

The ratio of V1/V2 of this invention is larger than 1.001. The preferred ratio is 1.01-6.0. The most preferred ratio is 1.5. The ratio of D1/D2 of this invention is larger than 1.001. The preferred ratio is 1.01-10. The more preferred ratio is 3-5. The most preferred ratio is 1.5.

The examples below are non-limiting and are merely representative of various aspects and features of the present invention.

EXAMPLE

Example 1

Surface Plasmon Resonance Curve Measurement

SPR Curve

Surface plasmon resonance curve could be described with five parameters, but the most common discussed parameters were surface plasmon resonance angle and half band width of surface plasmon resonance curve. X axis reflected the light intensity which measured by the signal photodiode division of the reference photodiode, Y axis was the scanning angle. When the laser beam scanned a particular angle, the energy was absorbed by the surface plasmon generated on the surface of the gold film. The wave vector of injection light matched the wave vector of surface plasmon. At this angle, the reflectance was minimum along the curve and closed to zero. The corresponding angle was the surface plasmon resonance angle. The surface plasmon resonance angle would decrease or increase with the refractive index of the sample. The smaller the refractive index was, the smaller the surface plasmon resonance angle was, and vice versa.

Setup Compartments

Translational Stage:

Produced by SIGMA company, catalog number was SGSP-120YAW (θz), was used to move the photodiodes. The least resolution of this translational stage was 0.005 degree.

Laser:

The light source used herein was produced by Melles Griot, Cylindrical Helium Neon Laser Systems Linear Polarization (25 LHP 213-249), red light of wavelength 632.8 nm, output with 0.5 mW.

Silicon Photodiode:

The two Silicon photodiode used herein were produced by HAKUTO, they were placed separately on the translational stage and used to measure the signal light intensity and reference light intensity.

Base:

The base was used to deposit Au with refractive index 1.75, material SF11.

Prism:

The prism was bought from Edmund, which size was in 15*21*15 mm and material was SFL11, catalog number H45-950 right angle prism.

Surface Plasmon Resonance Setup System

On setting up the surface plasmon resonance, a He—Ne laser (wavelength=632.8 nm) was used as the light source. The laser beam passed through the polarizer to block p-polarization from s-polarization component, and only p-polarization component could excite surface plasmon. The transmitted p-polarization beam was split into two beams via beam splitter (BS), one beam was detected by photodiode as reference light, and the other beam injected into prism at specific range of angles to decide surface plasmon angle. The reflected light was detected via the photodiode in the opposite side of prism as signal light. Surface plasmon was excited on Au metal film deposited on flat glass surface which attached on prism via matching oil. The current signal detected by photodiode was expanded via amplifier and transformed into voltage signal via 16-bit A/D converter (Adventech PCI-1716) The Y-axial represented the ratio of reference light and signal light, X-axial represented the incident angle of interface between prism and sample. Incident angle was controlled by controller which motor motorized stage with two arms. When surface plasmon resonance angle was detected, the energy of injected light was absorbed and surface plasmon resonance was achieved. This experimental setup was build by National Cheng-Kung University, department of Engineering Science, Adaptic Photonic Lab.

Gold Film

The gold film was provided by National Cheng-Kung University, department of Engineering Science, Adaptic Photonic Lab. The method used to deposit the gold film was High vacuum Electron beam evaporation. The thickness of the gold film was 47.5 nm, the base material was SF11 with refractive index 1.78.

Bacteria Preparation

JM 109 Strain

The bacteria used herein were JM109 strain, which was recA1 mutation that helped ensure insert stability. EndA1 mutation improved the quality of the plasmid miniprep DNA. HsdR17 mutation prevented the cleavage of cloned DNA by an endogenous endonuclease system.

Bacteria Incubation

Penicillin was referred to β-lactam drugs because of the importance of the β-lactam ring. An intact ting structure was essential for antibacterial activity. The cleavage of the ring by penicillinase (β-lactamase) inactivated the drug. The antibiotic bacteria strain used herein was transformed by ampicillin resistant plasmid that translated β-lactamase to cleave the ring of ampicillin. The bacteria was picked out by loop and planted in 5 ml LB broth over night, then transferred into 100 ml LB and incubated for two hours.

Example 2

System Sensitivity Test

In the system sensitivity test, different concentrations of sucrose solutions were made, and two programs to test the sensitivity of the surface plasmon resonance system was taken herein. Sucrose solution was used as a tool to test the sensitivity of the platform because the refractive index of sucrose solution has been identified. The relationship between refractive index and sucrose weight percentage solution was linearly.

The first program was the injection of five different weight percentages of sucrose solutions (1%, 2.5%, 5%, 7.5%, 10%) into the flow chamber. Different weight percentage solutions were changed when each of the solution reached the system balance.

The second program was the injection of the smaller concentration. Five different weight percentages of sucrose solutions (0.1%, 0.25%, 0.5%, 0.75%, 1%) were injected into the flow chamber. Different weight percentage solutions were changed when each of the solution reached the system balance.

Poly-L-lysine Coating

Poly-L-Lysine has been demonstrated as an effective tissue adhesive for use in various biochemistry procedures. Diluted Poly-L-Lysine solution with deionized water prior to coating slides. The flat glass surface deposited with Au metal film was immersed in poly-L-lysine solution (concentration is 200 ug) for at least 24 hours to interact with Au metal film, cells can be immobilized on biochips after incubation.

Example 3

Ampicillin Sensitivity and Resistance Test

The sterilized DI water was injected into the flow chamber for 30 min to stabilize the system when biochip coated with poly-L-lysine was assembled. After balancing, the incubated LA broth was injected into the flow chamber for 210 minutes to cover the AU metal film. Subsequently, antibiotic solution was injected, and the surface plasmon resonance curve was observed on the computer.

Figure 2:
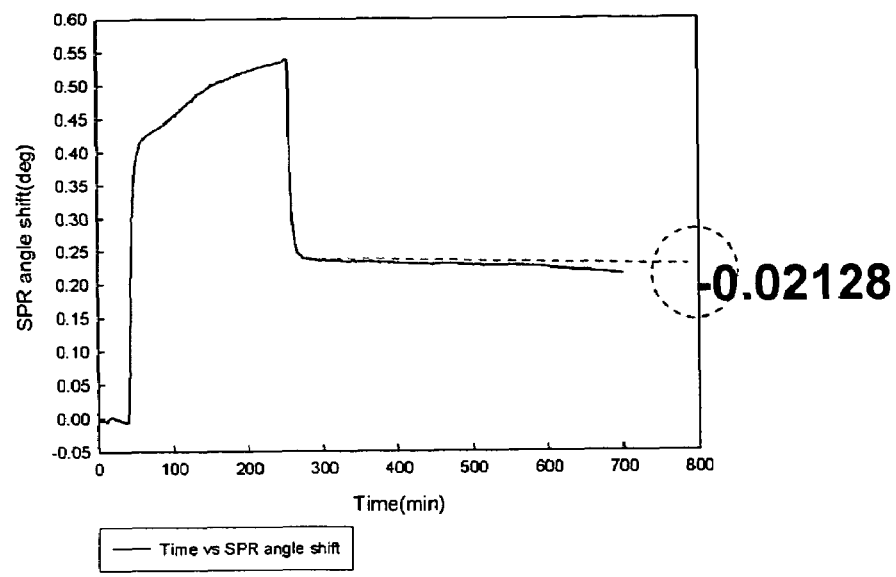
FIG. 2 shows the standard kinetic plot of SPR angle shift of ampicillin resistant strain.
Figure 3:
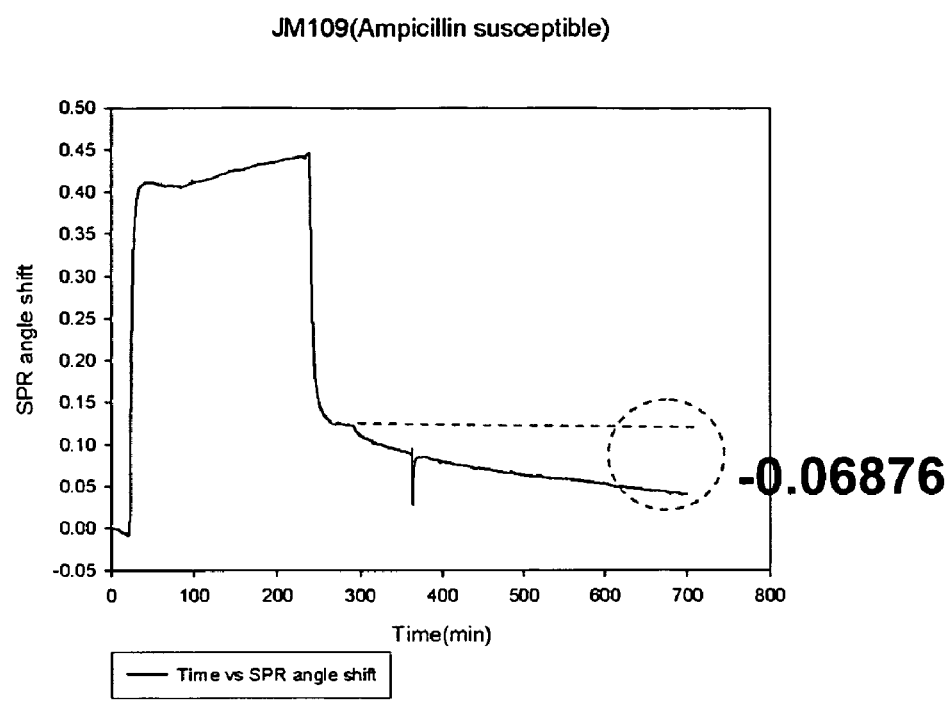
FIG. 3 shows the standard kinetic plot of SPR angle shift of ampicillin susceptible strain.

Surface plasmon resonance system measured SPR angle continuously, and compared SPR curve of antibiotic susceptible and antibiotic resistant strain under the same condition. The SPR curve of antibiotic resistant strain was depicted in FIG. 2, and antibiotic susceptible strain SPR curve was depicted in FIG. 3. Experimental data represented that after 30 minutes of balance of the SPR system, the injection of bacteria LB broth increased the SPR angle. After 210 minutes, the extra bacteria were washed with deionized water and presented the decrease of SPR angle, then balanced for 10-20 minutes. Antibiotic solution was injected after the balance curve. FIG. 3 can be figured out from the antibiotic susceptible strain. SPR angle had dramatically been dropped after approximately 30 minutes of the injection of antibiotics which indicated that the antibiotic destroyed the cell wall of bacteria and caused the breakdown of bacteria cell wall. The loosen structure of cell wall thus decreased the refractive index which shown on the computer was the decrease of SPR angle. The curve of antibiotic resistant did not measure the obvious drop of SPR angle. The drop of SPR angle indicated from antibiotic susceptible was −0.06876 degree which larger than −0.02128 degree when comparing to antibiotic resistant strain, approximately ⅓ times less.

TABLE 1

Repeated experiment data of comparing ampicillin susceptible
surface plasmon resonance angle shift with ampicillin resistant surface
plasmon resonance angle shift.

| Repeat result | Strain type | | |
|---|---|---|---|
| | Ampicillin susceptible surface plasmon resonance angle shift | Ampicillin resistant surface plasmon resonance angle shift | susceptible surface plasmon resonance angle shift/resistant surface plasmon resonance angle shift |
| 1st | −0.04909 | −0.02475 | 1.9834 |
| 2nd | −0.07286 | −0.0278 | 2.6208 |
| 3rd | −0.06876 | −0.02128 | 3.2312 |
| 4th | −0.0729 | −0.04355 | 1.6729 |
| Average | −0.0659 | −0.02935 | 2.377075 |
| Standard deviation | 0.11375 | 0.009837 | 0.692766 |

Figure 4:
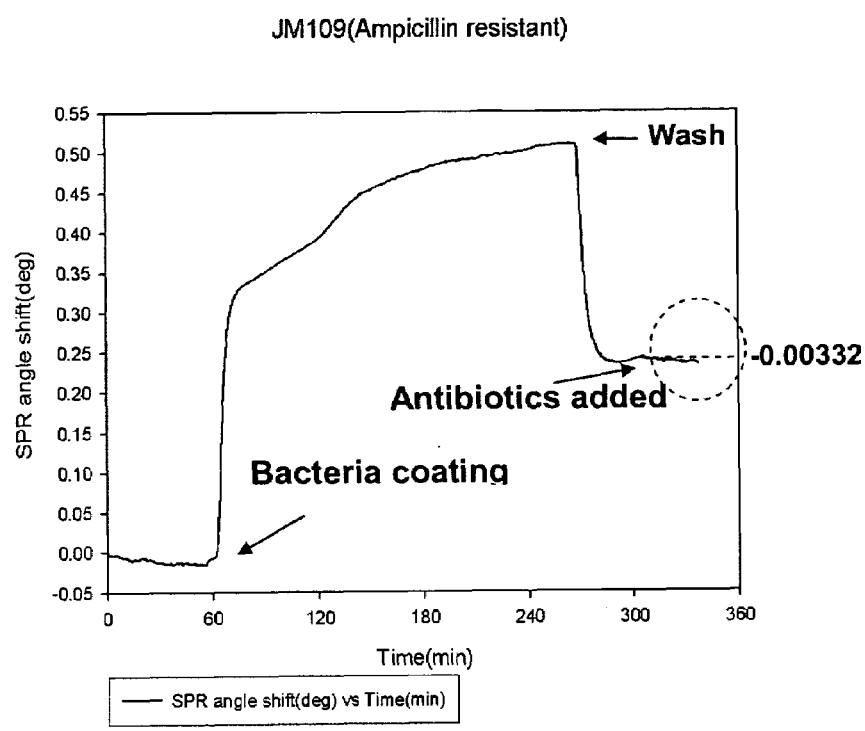
FIG. 4 shows the kinetic plot of SPR angle shift of ampicillin resistant strain treated with antibiotics for 30 min.
Figure 5:
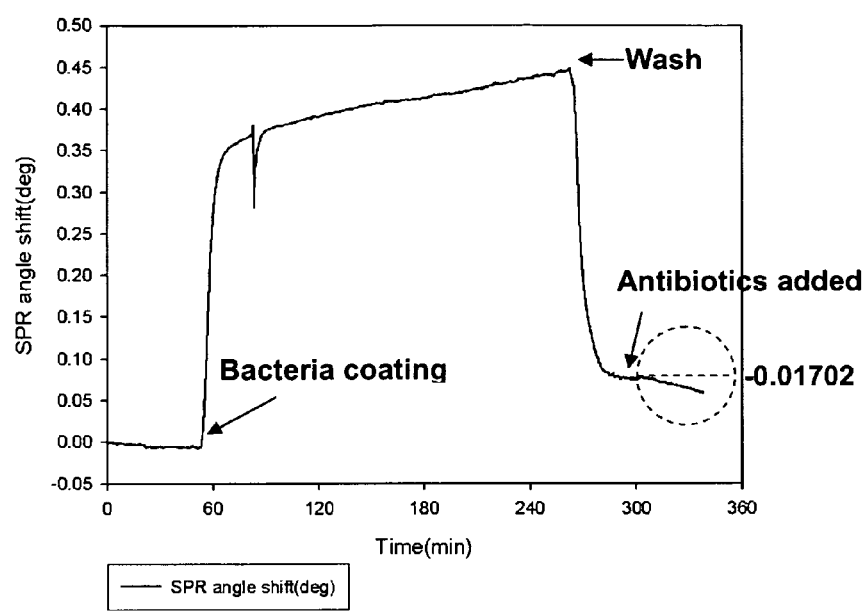
FIG. 5 shows the kinetic plot of SPR angle shift of ampicillin susceptible strain treated with antibiotics for 30 min.

There were shifts after a short time of antibiotic treatment, so the surface plasmon resonance curve continued thirty minutes after antibiotic treatment were measured. The curve could be figured out the comparison of the curve of antibiotic susceptible strain and antibiotic resistant strain (FIG. 4). The surface plasmon resonance curve of antibiotic susceptible strain had obvious decreased (FIG. 5). In that case, a conclusion could be made that at least thirty minutes later of antibiotic treatment, bacteria structure and morphology did change. This change could be detected by surface plasmon resonance system. The drop of SPR angle indicated from antibiotic susceptible was −0.01702 degree which larger than −0.00332 degree when comparing to antibiotic resistant strain, approximately ⅕ times less.

SEM (Scanning Electron Microscope)

Fixation

The cells were fixed with 2% glutaraldehyde in 0.02M PB solution (0.2M $NaH_2PO_4 \cdot H_2O$ 115 ml and 0.2M $Na_2HPO_4$ 385 ml, pH7.4) for one hour, and then rinsed two to three times with PBS solution (Nacl 8 g, Kcl 0.2 g, $Na_2HPO_4$ 1.44 g, and $KH_2PO_4$ 0.24 g in 1 L, pH7.4). After rinse with PBS solution, postfix with 2% $OsO_4$ solution for an hour. After rinsing with PBS solution two to three times, dehydrated in a graded series of ethanol including 50% ethanol for 10 minutes, 70% ethanol for 10 minutes, 90% ethanol for 10 minutes, and 100% ethanol 10 minutes for three times. The fixed samples were dried with Critical Point Dryer (Tousimis) and deposited gold for 120 seconds with Ion Sputter (JFC-1100).

SEM Scanning

SEM used a wolfram fiber or lantanhexaborid to produce electrons for thermo ionic emission. Then, they were accelerated toward the sample by using different potential of 2.5-50 kV. The electrons were directed toward one point by a system of lenses to produce an electronic ray spreading all over the sample. The incident electronic ray reacted with a sample generated several types of signals. The signals were then collected in detectors, and their output was multiplied to adjust intensity on CRT screen. The scanning electron microscope (JEOL JSM-5300, Japan) used herein had a magnification ranging from 15× to 200,000×.

Figure 6:
FIG. 6 shows the picture of *E. coli* without treating antibiotics.
Figure 7:
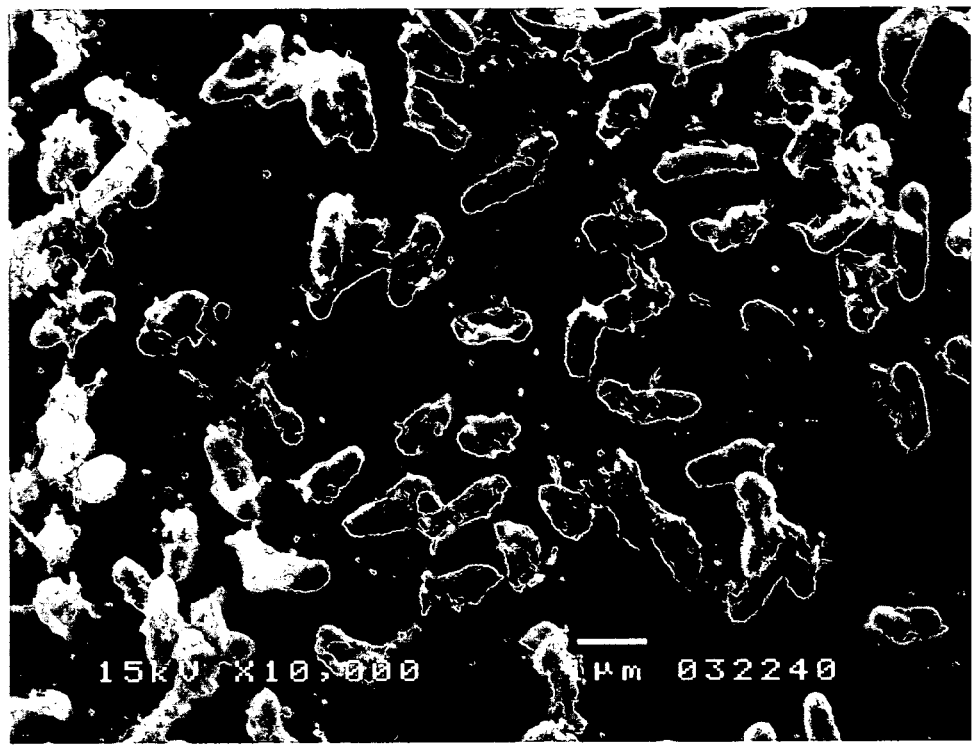
FIG. 7 shows the picture of ampicillin susceptible *E. coli* treated with 3 μg/ml antibiotics for 300 minutes.
Figure 8:
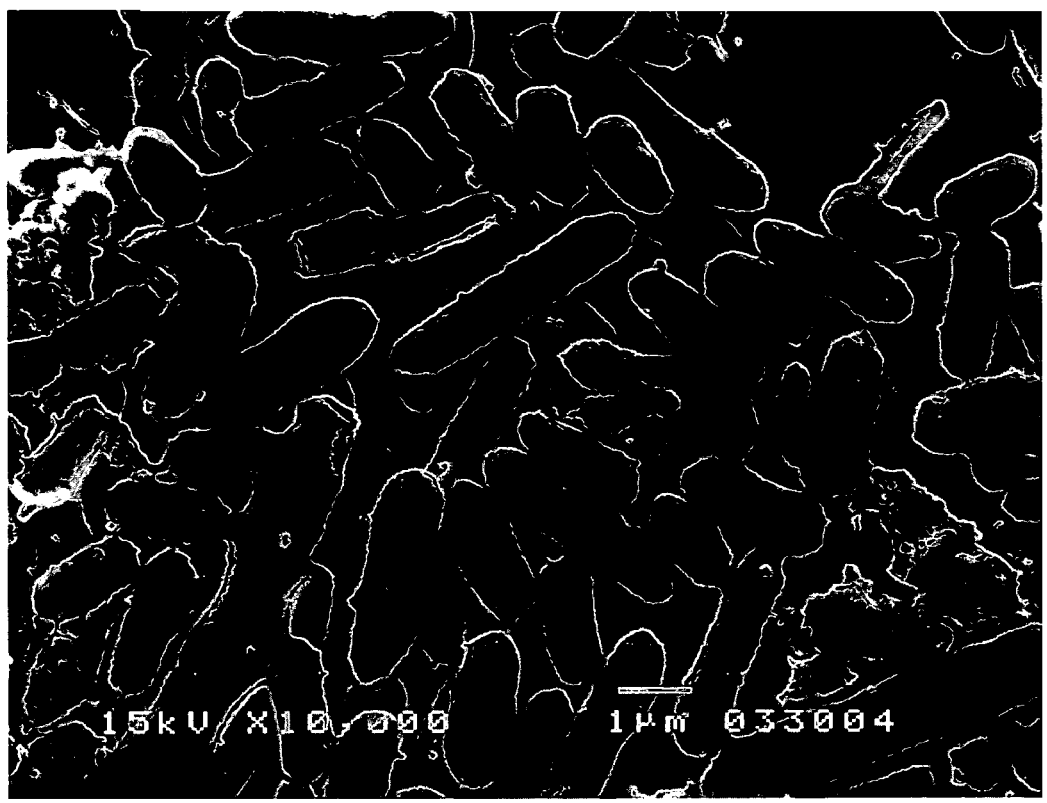
FIG. 8 shows the picture of ampicillin resistant *E. coli* treated with 3 μg/ml antibiotics for 300 minutes.

SEM scanning pictures of bacteria were shown in FIGS. 6, 7 and 8. The pictures could be figured out that antibiotic susceptible strain treated with ampicillin for 300 min had caused some damages on the bacteria. The shape of the bacteria had changed, but the SEM picture of ampicillin resistant strain resembled the SEM picture of bacteria that did not be treated with antibiotics.

Figure 9:
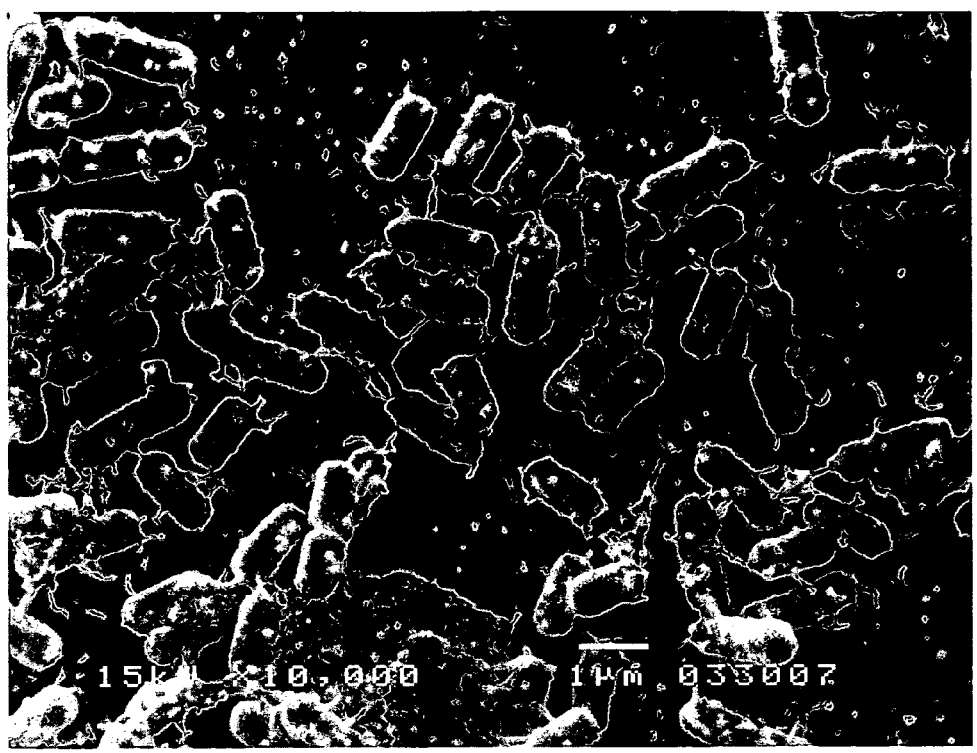
FIG. 9 shows the picture of ampicillin susceptible *E. coli* treated with 3 μg/ml antibiotics for 30 minutes.
Figure 10:
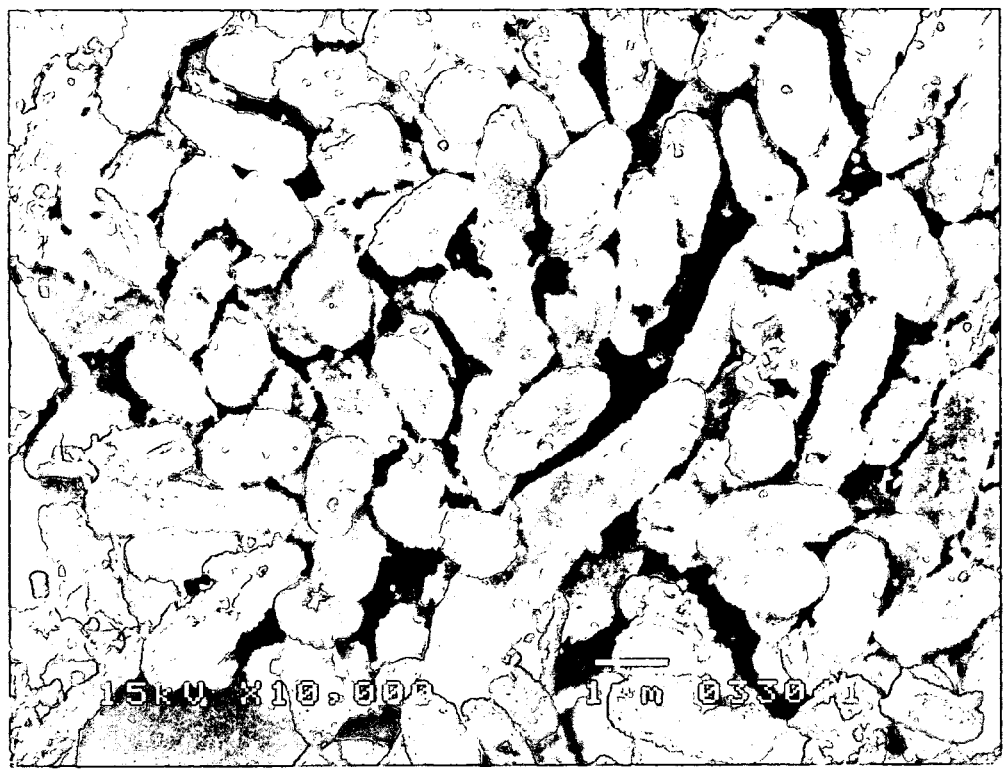
FIG. 10 shows the picture of ampicillin resistant *E coli* treated with 3 μg/ml antibiotics for 30 minutes.

FIGS. 9 and 10 were SEM scanning pictures of bacteria treated with ampicillin for thirty minutes. The pictures showed that there was not much difference on structure and morphology of bacteria between antibiotic susceptible and resistant strain after thirty minutes of antibiotic treatment. However, the SPR system could detect the slight change of the bacteria. Therefore, SPR system could be used on measuring of fast and tiny change.

Example 4

Tetracycline Sensitivity and Resistance Test

Figure 11:
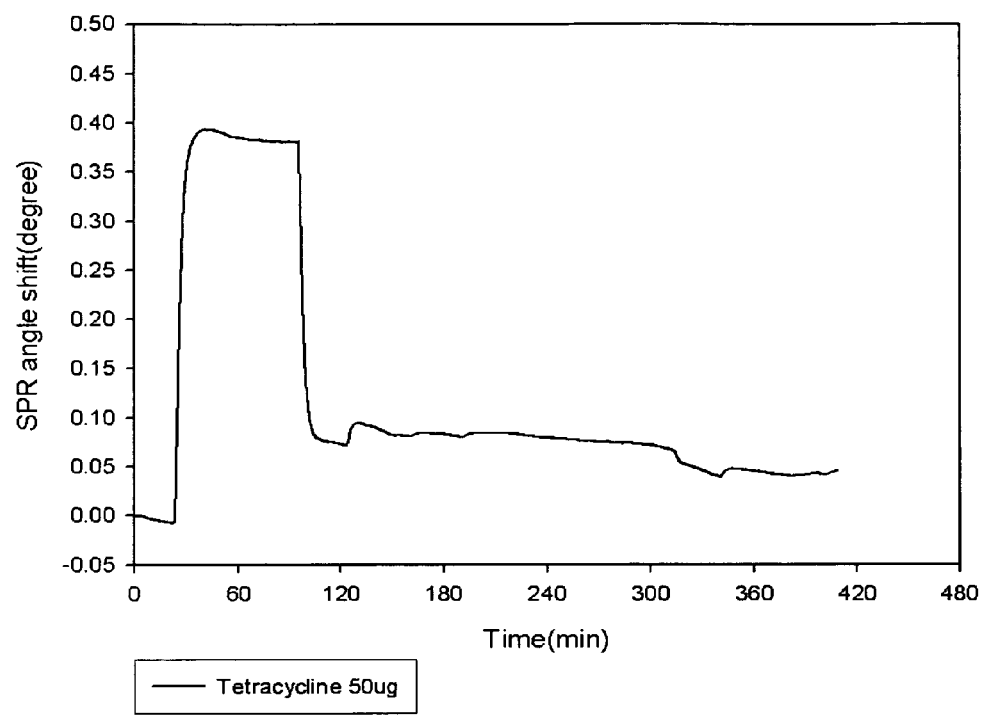
FIG. 11 shows the SPR angle shift of Tetracycline susceptible *S. epidermis* treated with 50 μg/ml antibiotics for 300 minutes.
Figure 12:
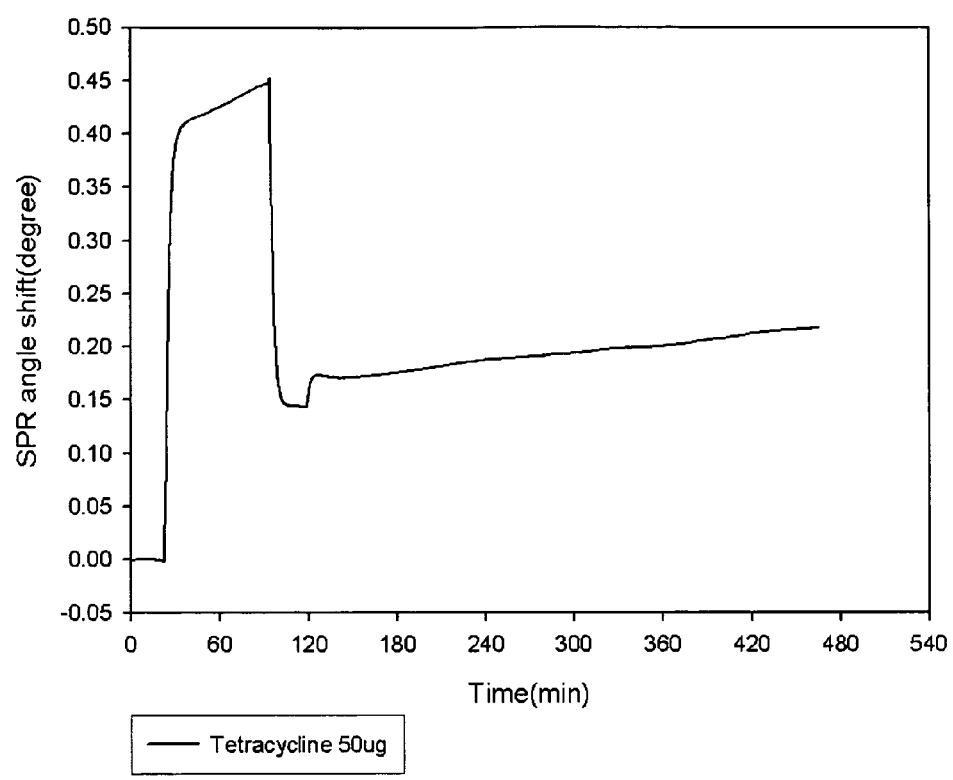
FIG. 12 shows the SPR angle shift of Tetracycline resistant *S. epidermis* treated with 50 μg/ml antibiotics for 300 minutes.
Figure 13:
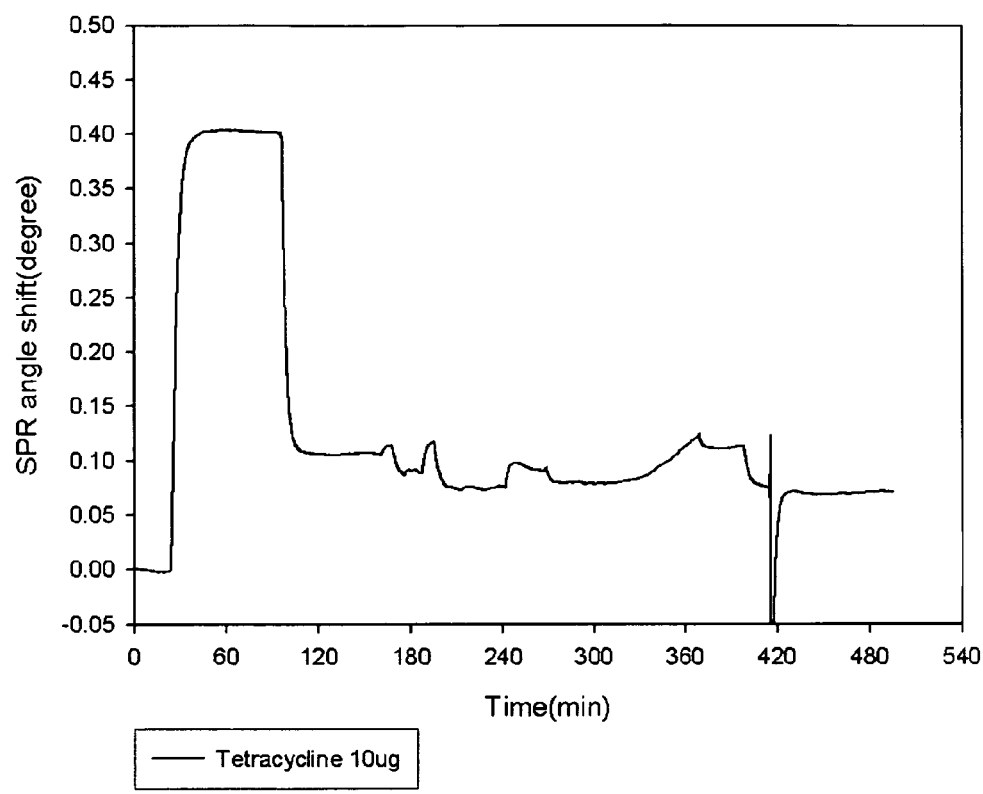
FIG. 13 shows the SPR angle shift of Tetracycline susceptible *S. epidermis* treated with 10 μg/ml antibiotics for 300 minutes.
Figure 14:
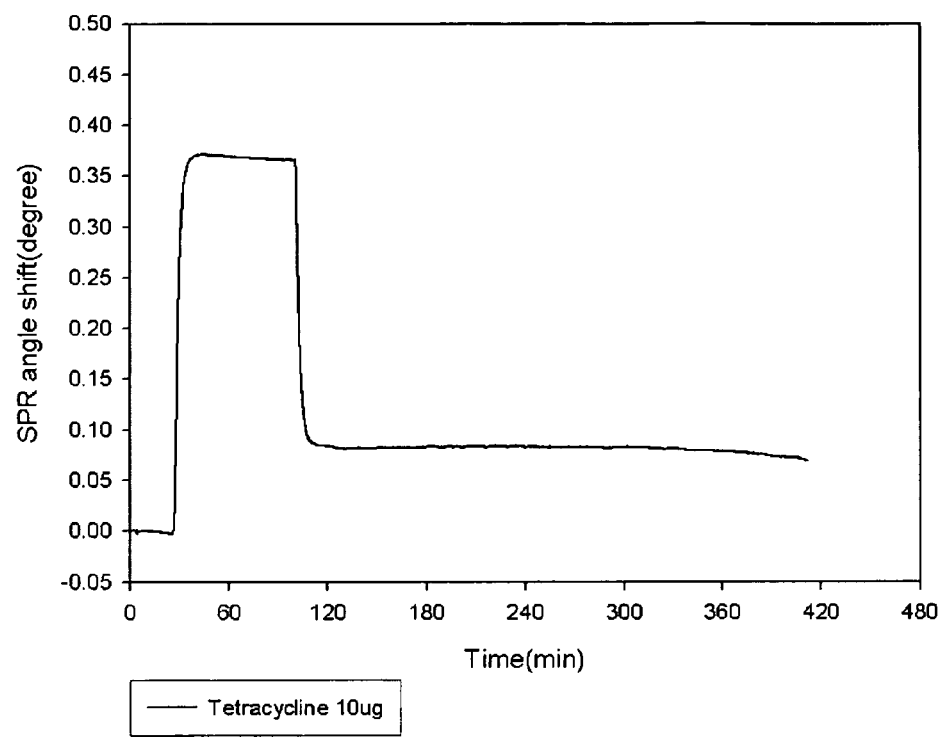
FIG. 14 shows the SPR angle shift of Tetracycline resistant *S. epidermis* treated with 10 μg/ml antibiotics for 300 minutes.

Like Example 3, *S. epidermis* was tested by tetracycline. The SPR curve of tetracycline susceptible strain treated with 50 μg/ml was depicted in FIG. 11, and the SPR curve of tetracycline resistant strain treated with 50 μg/ml was depicted in FIG. 12. The SPR curve of tetracycline susceptible strain treated with 10 μg/ml was depicted in FIG. 13, and the SPR curve of tetracycline resistant strain treated with 10 μg/ml was depicted in FIG. 14. As shown in FIGS. 13 and 14, about 30 minutes of 1 μg/ml tetracycline treatment, SPR curve of tetracycline susceptible strain had more obvious fluctuation than that of tetracycline resistant strain. As known in the art, the mechanism of tetracycline is to bind to 30S ribosomal subunit and prevents the amino-acyl tRNA from binding to the A site of the ribosome, and the influence of tetracycline to the cell wall is indirect in comparison with ampicillin. Given the above, it demonstrated that the shift of SPR angle for the susceptible strain was irregular but the shift of SPR angle for the resistant strain is smooth and monotonic over five hours. Such the different shifts of SPR angle were applied to identify susceptible strain and resistant strain.

One skilled in the art readily appreciates that the present invention is well adapted to carry out the objects and obtain the ends and advantages mentioned, as well as those inherent therein. The processes and methods for measuring antibiotic resistant organism are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of detecting a microorganism sensitive to a drug by a surface plasmon resonance device comprising (a) a prism coated with a metal film on the bottom of the prism or a metal film with grating, (b) a chamber for flowing through the microorganism wherein the chamber is contacted with the film, (c) an immobilized material coated on the inner layer of the chamber, (d) a light source which is projected on the film to generate an output light, (e) a light detector to receive the output light, and (f) a device to analysis surface plasmon resonance angle shift, the method comprises (1) providing a sample and a control group wherein the control group is drug susceptible or wild type, (2) flowing the control group and the sample through the chamber respectively to be captured by the immobilized material, (3) adding the drug into the chamber, (4) recording the data selected from the group consisting of (i) the value V1 of surface plasmon resonance angle shift of the control group and the value V2 of surface plasmon resonance angle shift of the sample, (ii) the value D1 of the drop of surface plasmon resonance angle shift of the control group and the value D2 of the drop of surface plasmon resonance angle shift of the sample, and (iii) the surface plasmon resonance angle shift of the control group and the sample, and (5) identifying the sample as drug resistance by the record selected from the group consisting of (I) ratio of V1/V2 larger than 1.001, (II) ratio of D1/D2 larger than 1.001, and (III) the surface plasmon resonance angle shift of the sample more smooth or monotonic than that of the control.

2. The method of claim 1 wherein the ratio of V1/V2 is 1.01-6.0.

3. The method of claim 1 wherein the ratio of V1/V2 is 1.67-3.23.

4. The method of claim 1 wherein the ratio of V1/V2 is 1.5.

5. The method of claim 1 wherein the ratio of D1/D2 is 1.01-10.

6. The method of claim 1 wherein the ratio of D1/D2 is 3-5.

7. The method of claim 1 wherein the ratio of D1/D2 is 1.5.

8. The method of claim 1 wherein the microorganism is bacteria or cell.

9. The method of claim 8 wherein the bacteria is *E. coli* or *Staphylococcus aureus*.

10. The method of claim 1 wherein the drug is penicillin, cephalosporin, ampicillin, chloramphenicol, tetracycline, sulfonamide or polymynix.

11. The method of claim 10 wherein the drug is ampicillin.

12. The method of claim 11 wherein the identification is determined by the record selected from the group consisting of (I) ratio of V1/V2 larger-than 1.001, and (II) ratio of D1/D2 larger than 1.001.

13. The method of claim 10 wherein the drug is tetracycline.

14. The method of claim 13 wherein the identification is determined by the surface plasmon resonance angle shift of the sample more smooth or monotonic than that of the control.

15. The method of claim 1 wherein the metal film is gold film.

16. The method of claim 1 wherein the immobilized material is poly-L-lysine, antibody or oligopeptide.

17. The method of claim 1 wherein the light source is He—Ne Laser with 632.8 nm wavelength.

* * * * *